US00PP31553P3

(12) United States Plant Patent
Arts

(10) Patent No.: US PP31,553 P3
(45) Date of Patent: Mar. 17, 2020

(54) RASPBERRY PLANT NAMED 'WENGI'

(50) Latin Name: *Rubus idaeus*
Varietal Denomination: Wengi

(71) Applicant: Niels Arts, Aalsmeer (NL)

(72) Inventor: Niels Arts, Aalsmeer (NL)

(73) Assignee: Allberry B.V., De Kwakel (NL)

( * ) Notice: Subject to any disclaimer, the term of this patent is extended or adjusted under 35 U.S.C. 154(b) by 0 days.

(21) Appl. No.: 15/732,919

(22) Filed: Jan. 13, 2018

(65) Prior Publication Data

US 2018/0220564 P1 Aug. 2, 2018

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
See application file for complete search history.

(56) References Cited

PUBLICATIONS

UPOV hit on raspberry plant named 'Wengi', QZ PBR 20170242, filed Jan. 27, 2017.*

* cited by examiner

*Primary Examiner* — Anne Marie Grunberg
(74) *Attorney, Agent, or Firm* — C. A. Whealy

(57) ABSTRACT

A new and distinct cultivar of Raspberry plant named 'Wengi', characterized by its upright and somewhat bushy plant habit; freely branching habit; high fruit production; fruits are produced on prior and current seasons' canes; large red purple-colored broadly conical fruits; pleasant and sweet fruit taste; and good fruit postharvest longevity.

2 Drawing Sheets

Botanical designation: *Rubus idaeus.*
Cultivar denomination: 'WENGI'.

BACKGROUND OF THE INVENTION

The present Invention relates to a new and distinct cultivar of Raspberry plant, botanically known as *Rubus idaeus* and hereinafter referred to by the name 'Wengi'.

The new Raspberry plant is a product of a planned breeding program conducted by the Inventor in Rossum, Gelderland, The Netherlands. The objective of the breeding program was to develop new Raspberry plants with good fruit quality, productivity, uniformity and postproduction longevity.

The new Raspberry plant originated from a cross-pollination made by the Inventor of two unidentified selections of *Rubus idaeus*, not patented. Seed was collected from a number of potential parent plants, combined and sown. The new Raspberry plant was discovered and selected by the Inventor as a single plant from within the progeny of the stated cross-pollination in a controlled environment in Rossum, Gelderland, The Netherlands in early September, 2011.

Asexual reproduction of the new Raspberry plant by root cuttings in a controlled environment at Rossum, Gelderland, The Netherlands since the spring of 2012 has shown that the unique features of this new Raspberry plant are stable and reproduced true to type in successive generations of asexual reproduction.

SUMMARY OF THE INVENTION

Plants of the new Raspberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Wengi'. These characteristics in combination distinguish 'Wengi' as a new and distinct Raspberry plant:

1. Upright and somewhat bushy plant habit.
2. Freely branching habit.
3. High fruit production.
4. Fruits are produced on prior and current seasons' canes.
5. Large red purple-colored broadly conical fruits.
6. Pleasant and sweet fruit taste.
7. Good fruit postharvest longevity; fruits do not darken in color after harvesting.

Plants of the new Raspberry can be compared to plants of *Rubus idaeus* 'Advabertwee', disclosed in U.S. Reissue Pat. No. 46,030 and U.S. Plant Pat. No. 23,914. In side-by-side comparisons, plants of the new Raspberry differ from plants of 'Advabertwee' in the following characteristics:

1. Plants of the new Raspberry grow faster than plants of 'Advabertwee'.
2. Plants of the new Raspberry flower and fruit earlier than plants of 'Advabertwee'.
3. Plants of the new Raspberry have slightly smaller fruits than plants of 'Advabertwee'.

BRIEF DESCRIPTION OF THE PHOTOGRAPHS

The accompanying colored photographs illustrate the appearance of the new Raspberry plant showing the colors as true as it is reasonably possible to obtain in colored reproductions of this type. Colors in the photographs may differ slightly from the color values cited in the detailed botanical description which accurately describe the colors of the new Raspberry plant.

The photograph on the first sheet is a side perspective view of typical fruiting plants of 'Wengi'.

The photograph on the second sheet is a close-up view of typical fruits of 'Wengi'.

DETAILED BOTANICAL DESCRIPTION

The aforementioned photographs, following observations and measurements describe plants grown during the spring, summer and autumn in 10-liter containers in a polyethylene-covered greenhouse in Rossum, The Netherlands and under typical cultural practices of Raspberry plant production. During the production of the plants, day temperatures averaged 17° C. and night temperatures averaged 11° C. Plants were one year old when the photograph and description were taken. In the following description, color references are made to The Royal Horticultural Society Colour Chart, 1995 Edition, except where general terms of ordinary dictionary significance are used.

Botanical classification: *Rubus idaeus* 'Wengi'.

Parentage:

- *Female, or seed, parent*.—Unidentified selection of *Rubus idaeus*, not patented.
- *Male, or pollen, parent*.—Unidentified selection of *Rubus idaeus*, not patented.

Propagation:

- *Type*.—By root cuttings.
- *Time to initiate roots, summer*.—About 12 to 14 days at temperatures about 15° C. to 17° C.
- *Time to produce a rooted young plant, summer*.—About six weeks at temperatures about 15° C. to 17° C.
- *Root description*.—Medium to thin in thickness, fibrous, typically brownish white brown in color, actual color of the roots is dependent on substrate composition, water quality, fertilizer type and formulation, substrate temperature and physiological age of roots.
- *Rooting habit*.—Freely branching; dense.

Plant description:

- *Plant and growth habit*.—Upright and somewhat bushy plant habit; vigorous growth habit; rapid growth rate.
- *Plant height*.—About 1.8 to 2 meters.
- *Plant diameter*.—About 40 cm.

Cane description:

- *Prior season's canes*.—Length: About 120 cm. Internode length: About 6 cm. Color: Close to 164B to 164C, no anthocyanin observed. Time of vegetative bud burst: Mid to late March in The Netherlands. Length of vegetative bud: About 6 mm. Time of cane emergence: Early April in The Netherlands.
- *Current season's canes*.—Length: About 210 cm. Internode length: About 6 cm. Color: Close to 143C, no anthocyanin observed. Time of vegetative bud burst: Early March in The Netherlands. Length of vegetative bud: About 1 cm. Time of cane emergence: April in The Netherlands.
- *Strength*.—Strong.
- *Aspect*.—Mostly erect.
- *Texture*.—Smooth, glabrous; thorny.
- *Color, developing*.—Close to 145B.
- *Color, dormant*.—Close to 176B.
- *Thorns*.—Density: About four per linear cm. Length: About 2 mm. Width: About 3 mm. Shape: Roughly deltoid. Apex: Acuminate, downwardly sloping. Base: Truncate. Margin: Entire. Color, immature and mature: Close to 183A.

Leaf description:

- *Arrangement*.—Alternate; compound with typically three to five leaflets.
- *Length, leaf*.—About 24 cm to 34 cm.
- *Width, leaf*.—About 18 cm to 24 cm.
- *Length, terminal leaflet*.—About 13 cm to 18 cm.
- *Width, terminal leaflet*.—About 9 cm to 14 cm.
- *Length, lateral leaflets*.—About 9 cm to 16 cm.
- *Width, lateral leaflets*.—About 6 cm to 11 cm.
- *Leaflet shape*.—Ovate; not overlapping.
- *Leaflet apex*.—Cuspidate.
- *Leaflet base*.—Cordate.
- *Leaflet margin*.—Double serrate.
- *Leaflet profile*.—Straight.
- *Leaflet texture, upper and lower surfaces*.—Smooth, glabrous; rugose.
- *Leaflet venation*.—Pinnate.
- *Leaflet color*.—Developing leaflets, upper surface: Close to 145A. Developing leaflets, lower surface: Close to 146B. Fully expanded leaflets, upper surface: Close to 146A; venation, close to 146A. Fully expanded leaflets, lower surface: Close to 147C; venation, close to 147D.
- *Petioles*.—Length, leaf: About 6 cm to 7 cm. Diameter, leaf: About 3 mm. Length, terminal leaflet: About 3 cm. Diameter, terminal leaflet: About 3 mm. Length, lateral leaflets: About 3 mm. Diameter, lateral leaflets: About 3 mm. Texture, upper and lower surfaces: Sparsely prickled. Color, upper and lower surfaces: Close to 145C.

Flower description:

- *Flower form and flowering habit*.—Single star-shaped flowers arranged in axillary sprays; freely flowering with about three to seven flowers per spray and about seven to eight sprays per lateral branch; flowers face mostly outwardly; flowers not persistent.
- *Fragrance*.—None detected.
- *Natural flowering season*.—In The Netherlands, plants flower mid to late April on prior season's canes and in July on current season's canes.
- *Flower buds*.—Length: About 5 mm to 10 mm. Diameter: About 5 mm to 10 mm. Shape: Roughly deltoid with acuminate apex. Color: Close to 141D.
- *Flower diameter*.—About 1.8 cm.
- *Flower depth (height)*.—About 5 mm.
- *Petals*.—Arrangement: Single whorl of five petals. Length: About 9 mm to 10 mm. Width: About 4 mm to 5 mm. Shape: Lanceolate to slightly ovate. Apex: Obtuse. Base: Attenuate. Margin: Entire. Texture, upper and lower surfaces: Smooth, glabrous. Color: When opening and fully opened, upper surface: Close to 155D. When opening and fully opened, lower surface: Close to 155D.
- *Sepals*.—Arrangement: Single whorl of five sepals forming a star-shaped calyx. Calyx length: About 2 cm to 2.5 cm. Calyx width: About 2 cm to 2.5 cm. Length: About 2 cm. Width: Proximally, about 1 cm; distally, about 2 mm. Shape: Deltoid. Apex: Acuminate. Margin: Entire. Texture, upper and lower surfaces: Slightly pubescent. Color: When developing, upper and lower surfaces: Close to 145B. Fully opened, upper and lower surfaces: Close to 145B.

*Peduncles*.—Length: About 5 cm to 10 cm. Diameter: About 1.5 mm. Strength: Strong. Aspect: About 30° from vertical. Texture: Prickled. Color: Close to 145A; no anthocyanin observed.

*Pedicels* (*flowers and fruits*).—Length: About 3 cm to 5 cm. Diameter: About 1.5 mm. Strength: Strong. Aspect: About 30° from peduncle axis. Texture: Prickled. Color: Close to 145B; no anthocyanin observed.

*Reproductive organs*.—Stamens: Quantity per flower: About 50 or more. Filament color: Close to 155D. Anther length: About 1 mm. Anther color: Close to 164C and 156C. Pollen color: Close to 196C. Pistils: Quantity per flower: About 80 to 100. Pistil length: About 5 mm. Stigma shape: Rounded. Stigma color: Close to 155D. Style length: About 5 mm. Style color: Close to 155D. Receptacles: Height: About 1 cm. Diameter: About 1 cm. Shape: Conical. Color: Close to 155D. Fruits (aggregate of drupelets): Quantity: One per flower. Length of fruiting lateral: About 60 cm on prior season's canes, about 70 cm on current season's canes. Fruiting lateral aspect: About 45° from vertical on prior season's canes, and about 60° from vertical on current season's canes. Number of drupelets per fruit: About 90 to 120. Time of fruit ripening: In The Netherlands, on prior season's canes, fruits ripen in mid May, and on current season's canes, fruits ripen in September. Length of fruiting period: In The Netherlands, on prior season's canes, fruits are produced for about eight weeks, and on a current season's canes, fruits are produced for about 56 to 60 days. Length: About 2 cm to 2.2 cm, fruits produced on prior season's canes are slightly larger than fruits produced on current seasons's canes. Diameter: About 1.8 cm to 2.2 cm. Shape: Broadly conical. Weight: About 6 to 7 grams. Firmness: Firm. Taste: Pleasant, sweet. Luster: Glossy. Adherence to plug: Moderately strong on both prior and current season's canes. Postharvest longevity: Good postharvest longevity, fruits last up to eleven days; fruits do not darken in color after harvest. Color: Close to 58A, 58B and 61B. Seeds: Quantity: One per drupelet. Length: About 2.5 mm. Diameter: About 1 mm. Texture: Smooth, glabrous. Color: Close to 20D.

Pathogen & pest resistance: Plants of the new Raspberry have been noted to be resistant to Downy Mildew (*Peronospora sparsa*) and Red Spider Mites (*Tetranychus urticae*).

Temperature tolerance: Plants of the new Raspberry have been observed to tolerate temperatures ranging from 4° C. to 35° C.

It is claimed:

1. A new and distinct Raspberry plant named 'Wengi' as illustrated and described.

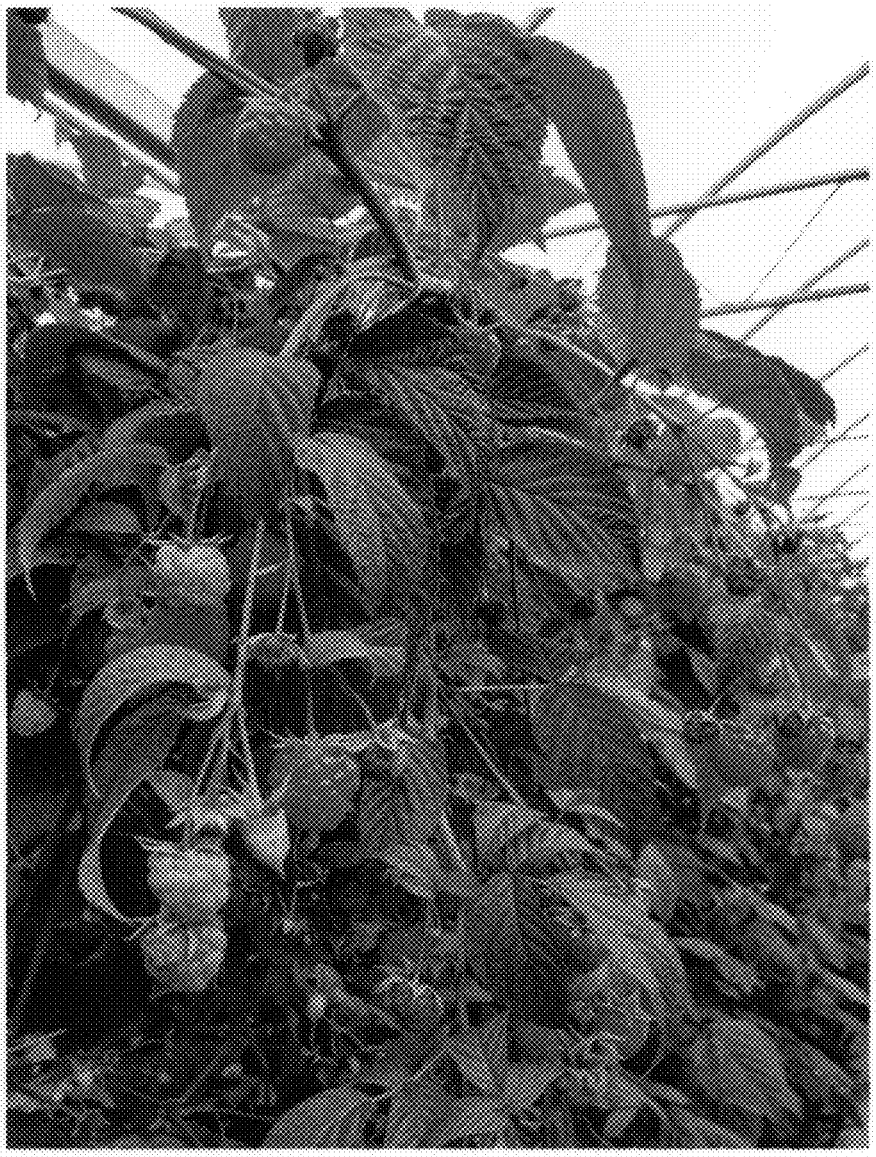

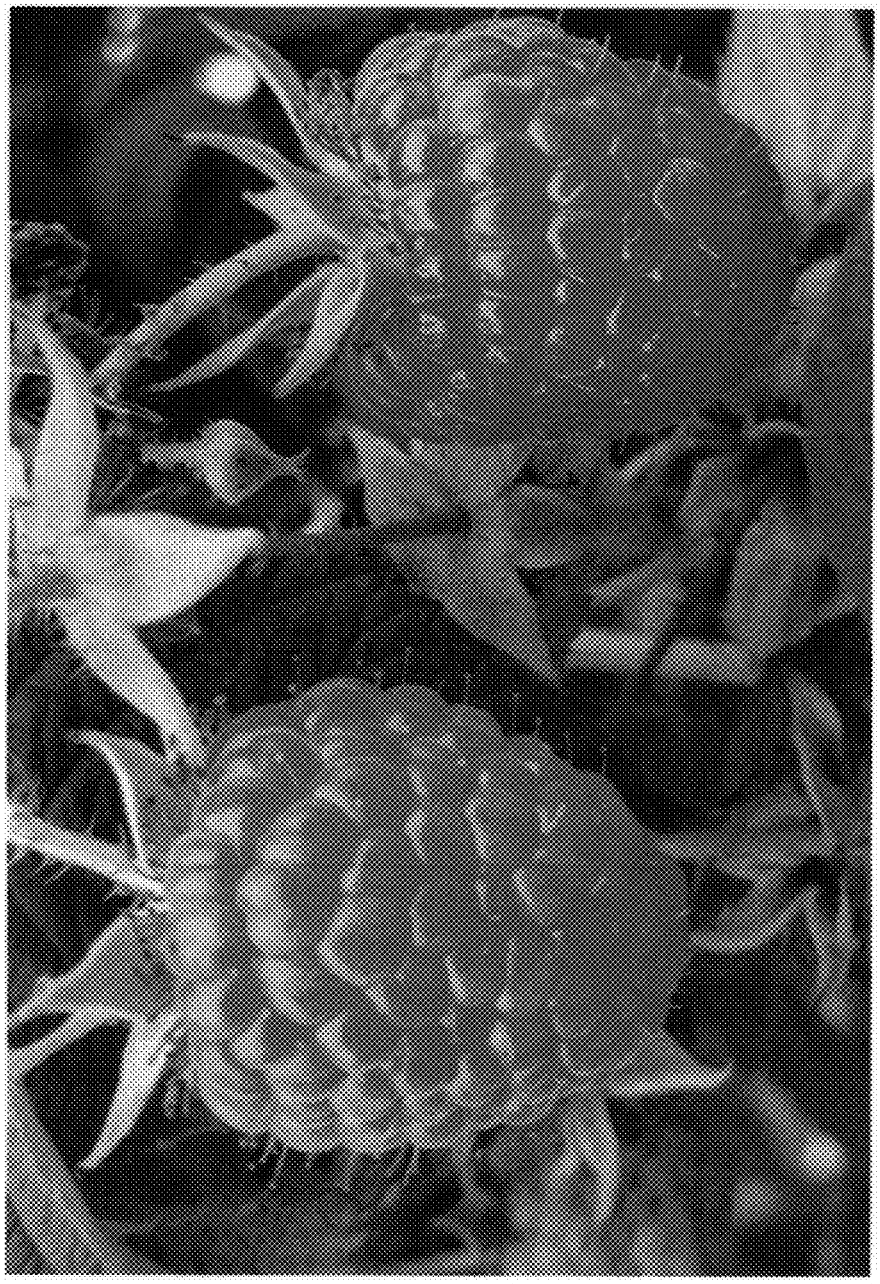

* * * * *